(12) United States Patent
Lam et al.

(10) Patent No.: US 8,895,055 B2
(45) Date of Patent: Nov. 25, 2014

(54) TELODENDRIMER NANODISCS WITHOUT APOLIPOPROTEIN

(71) Applicant: The Regents of the University of California, Oakland, CA (US)

(72) Inventors: Kit S. Lam, Davis, CA (US); Juntao Luo, Jamesville, NY (US); Joyce S. Lee, Elk Grove, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/719,766

(22) Filed: Dec. 19, 2012

(65) Prior Publication Data
US 2013/0164369 A1    Jun. 27, 2013

Related U.S. Application Data

(60) Provisional application No. 61/578,568, filed on Dec. 21, 2011.

(51) Int. Cl.
*A61K 9/127*    (2006.01)
*A61K 31/7048*    (2006.01)

(52) U.S. Cl.
CPC ........... *A61K 9/1271* (2013.01); *A61K 31/7048* (2013.01); *A61K 9/1275* (2013.01)
USPC ................................. 424/450; 514/34; 514/31

(58) Field of Classification Search
None
See application file for complete search history.

(56) References Cited

U.S. PATENT DOCUMENTS

| | | | |
|---|---|---|---|
| 6,365,191 B1 | 4/2002 | Burman et al. | |
| 7,824,709 B2 * | 11/2010 | Ryan et al. | 424/489 |
| 2002/0041898 A1 | 4/2002 | Unger et al. | |
| 2006/0013885 A1 | 1/2006 | Nah et al. | |
| 2006/0127310 A1 | 6/2006 | Russell-Jones et al. | |
| 2008/0188399 A1 | 8/2008 | Sinko et al. | |
| 2009/0203706 A1 | 8/2009 | Zhao et al. | |
| 2010/0158994 A1* | 6/2010 | Watkin | 424/450 |
| 2011/0286915 A1 | 11/2011 | Lam et al. | |

FOREIGN PATENT DOCUMENTS

| | | |
|---|---|---|
| WO | 99/59550 A1 | 11/1999 |
| WO | WO-2010-039496  * | 8/2010 |

OTHER PUBLICATIONS

Xiao K, PEG oligocholic acid telodendrimer micelles for the targeted delivery of doxorubicin to B cell lymphoma, JCR, 2011, 155, 272-281.*
Chen, et al., "Fluorescence Study of Inclusion Complexes between Star-Shaped Cholic Acid Derivatives and Polycyclic Aromatic Fluorescent Probes and the Size Effects of Host and Guest Molecules," *Journal of Physical Chemistry*, vol. 112, No. 11, pp. 3402-3409 (2008).
Duncan, "Dawning Era of Polymer Therapeutics," *Nature Rev. Drug. Discov.*, vol. 2, No. 5, 347-360 (2003).
Gref, et al., "Biodegradable Long-Circulating Polymeric Nanospheres," *Science American Association for the Advancement of Science*, vol. 263, No. 5153, pp. 1600-1603 (1994).
Li, et al., "Antimicrobial Activities of Amine- and Guanidine-Functionalized Cholic Acid Derivatives," *Antimicrobial Agents and Chemotherapy*, vol. 43(6), pp. 1347-1349 (Jun. 1999).
Luo, et al., "Asymmetric Poly(ethylene glycol) Star Polymers with a Cholic Acid Core and Their Aggregation Properties," *Biomacromolecules*, vol. 10, No. 4, pp. 900-906 (2009).
Xiao, et al., "A self-assembling nanoparticle for paclitaxel delivery in ovarian cancer," *Biomaterials*, vol. 30, No. 30, pp. 6006-6016 (2009).
Vijayalakshmi, et al., "A Simple Construction of a Bile Acid Based Dendritic Light Harvesting System," *Organic Letters*, vol. 7, No. 13, pp. 2727-2730 (2005).
International Search Report and Written Opinion for PCT/US2009/057852, 19 pages, mailed on May 6, 2010.
International Search Report and Written Opinion for PCT/US12/70508, 11 pages, mailed on Feb. 27, 2013.

* cited by examiner

*Primary Examiner* — Frederick Krass
*Assistant Examiner* — Celeste A Roney
(74) *Attorney, Agent, or Firm* — Kilpatrick Townsend and Stockton LLP

(57) ABSTRACT

The present invention provides a nanodisc without a membrane scaffold protein. The nanodisc includes a telodendrimer and a lipid; the nanodisc does not include a membrane scaffold protein. The telodendrimer has the general formula PEG-L-D-(R)$_n$, wherein D is a dendritic polymer; L is a bond or a linker linked to the focal point group of the dendritic polymer; each PEG is a poly(ethylene glycol) polymer; each R is and end group of the dendritic polymer, or and end group with a covalently bound hydrophobic group, hydrophilic group, amphiphilic compound, or drug; and subscript n is an integer from 2 to 20. Methods of making the nanodiscs are also provided.

21 Claims, 7 Drawing Sheets

Figure 1

| Lipid | Name | Structure | $T_m$ | MW | Carbon # |
|---|---|---|---|---|---|
| DPPC | 1,2-dihexadecanoyl-sn-glycero-3-phosphocholine | 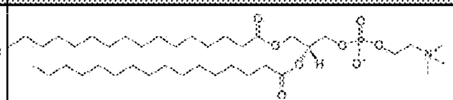 | 41°C | 734.04 | 16:0/16:0 |
| DMPC | 1,2-ditetradecanoyl-sn-glycero-3-phosphocholine | 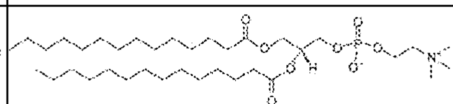 | 23°C | 677.93 | 14:0/14:0 |
| MPPC | 1-tetradecanoyl-2-hexadecanoyl-sn-glycero-3-phosphocholine | 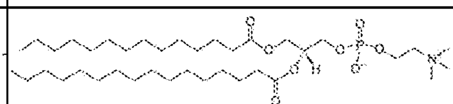 | 35°C | 705.98 | 14:0/16:0 |
| DSPC | 1,2-dioctadecanoyl-sn-glycero-3-phosphocholine | 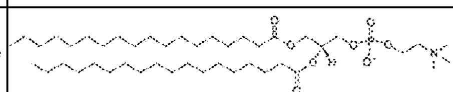 | 55°C | 790.15 | 18:0/18:0 |
| DSPE | 1,2-distearoyl-sn-glycero-3-phosphoethanolamine | 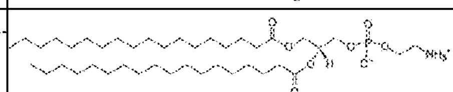 | 74°C | 748.06 | 18:0/18:0 |
| DPPE | 1,2-dihexadecanoyl-sn-glycero-3-phosphoethanolamine | 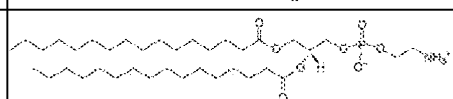 | 63°C | 691.96 | 16:0/16:0 |
| DSPG | 1,2-distearoyl-sn-glycero-3-phospho-(1'-rac-glycerol) | 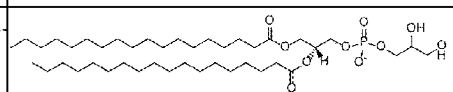 | 55°C | 801.06 | 18:0/18:0 |
| DPPG | 1,2-dipalmitoyl-sn-glycero-3-phospho-(1'-rac-glycerol) | 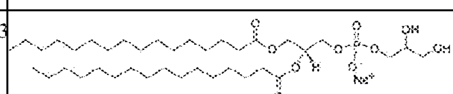 | 41°C | 744.95 | 16:0/16:0 |
| Chol | Cholesterol | 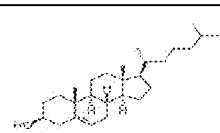 | 148.5° | 400.64 | n/a |

Figure 2
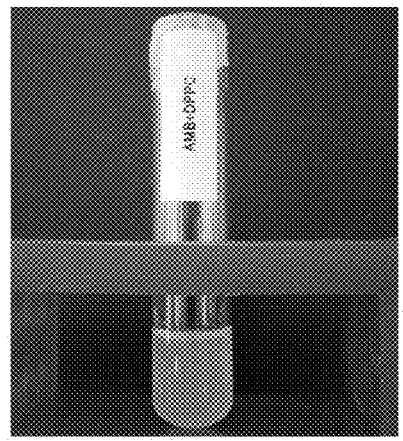
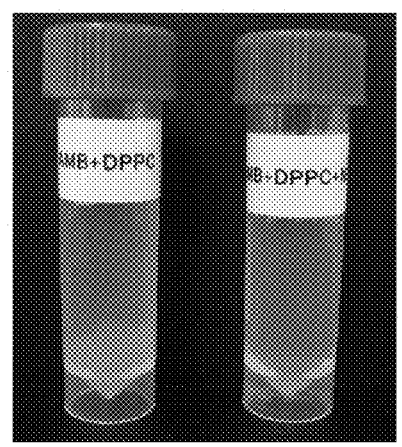
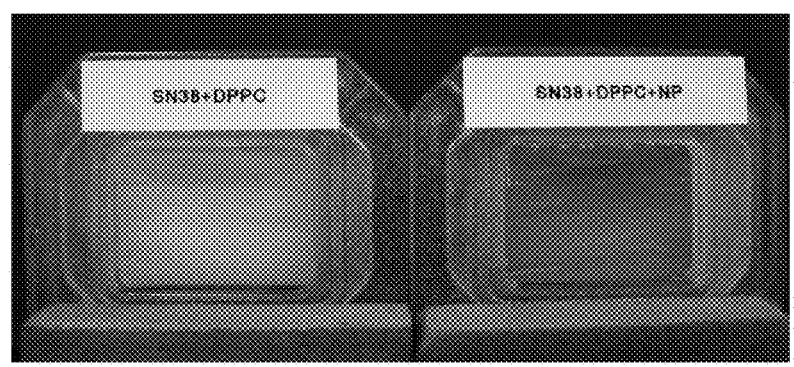

Figure 3
A
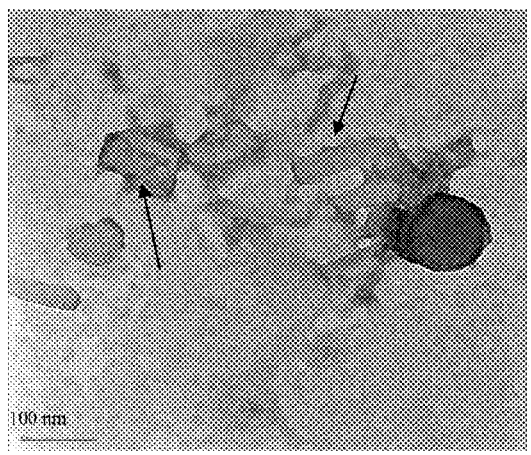
B
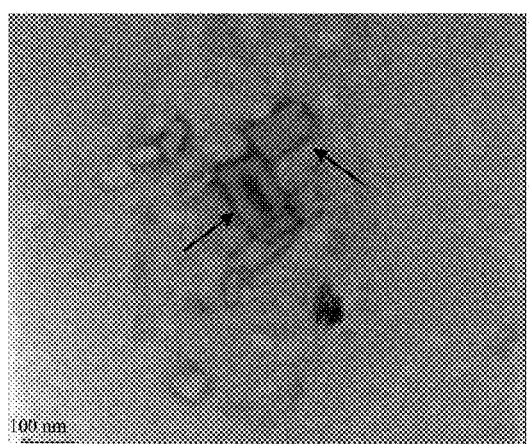
C
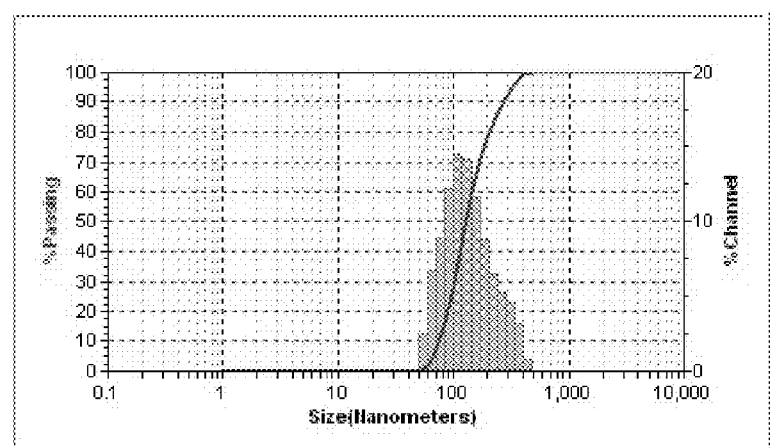

Figure 4
A
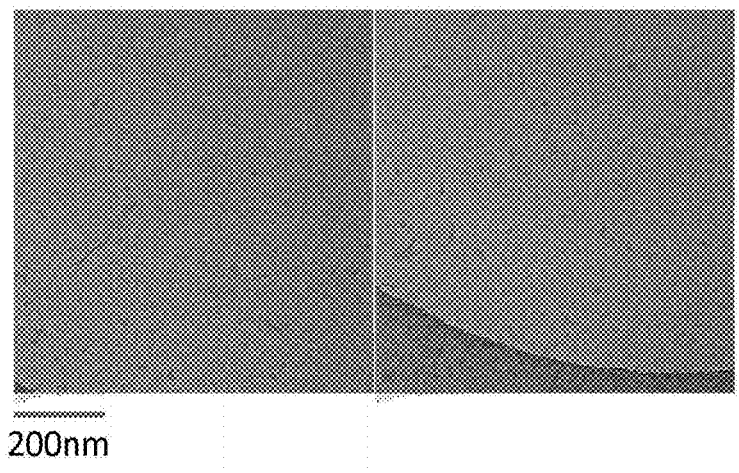
B
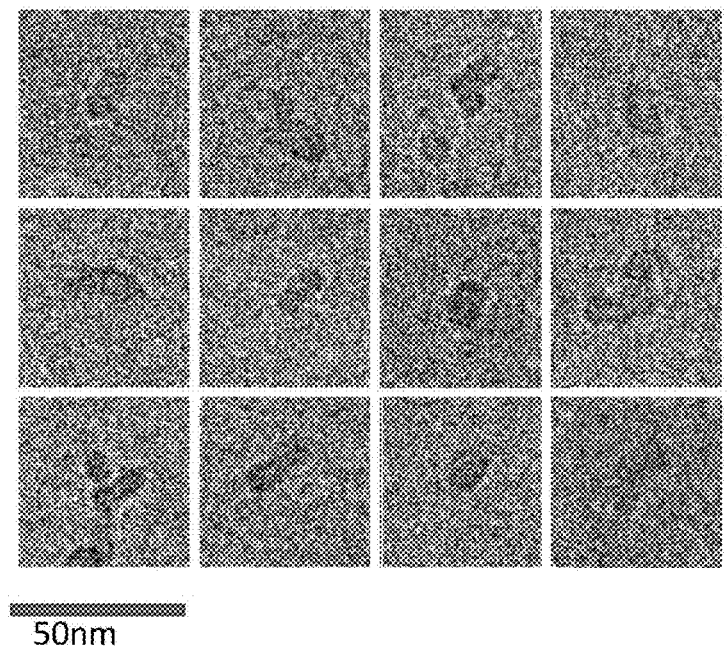

Figure 5
A
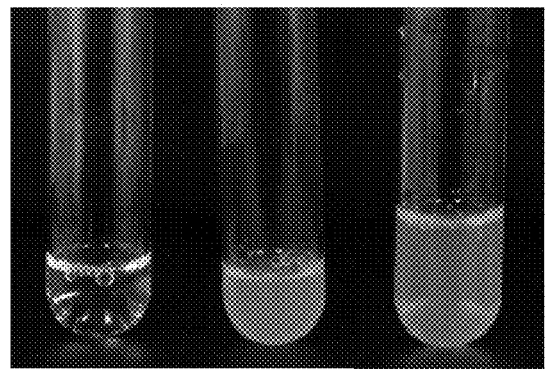
B
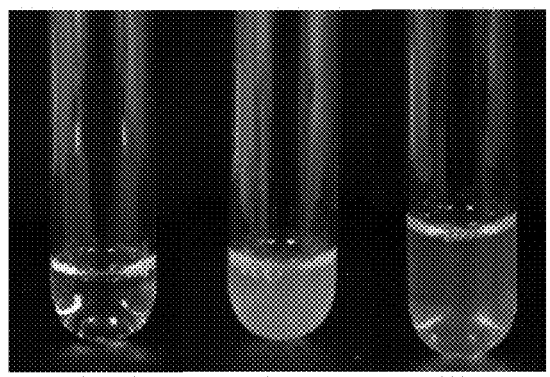
C
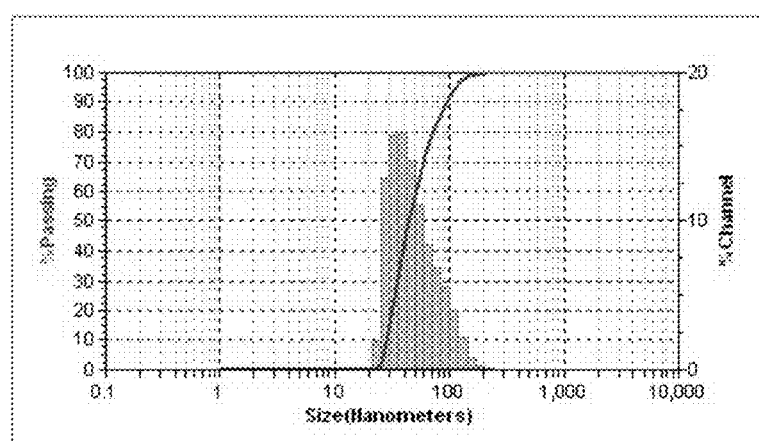

Figure 6
A
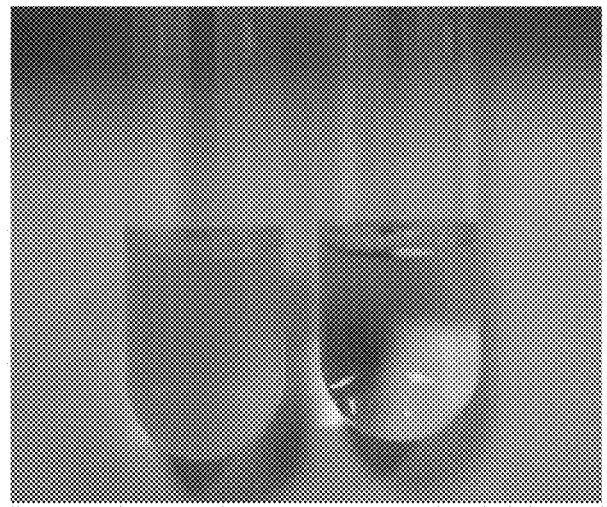
B
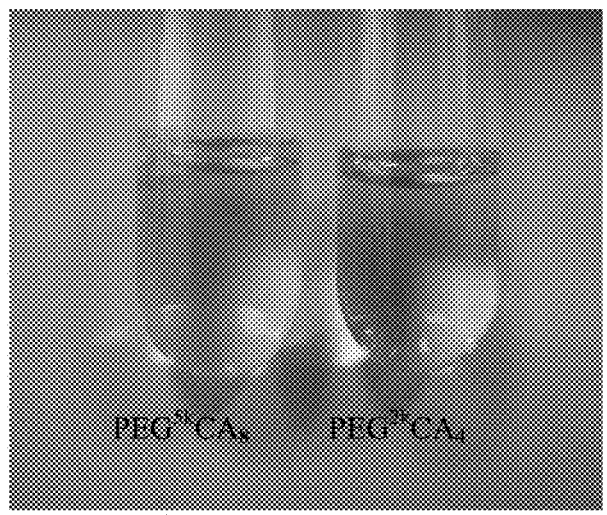

US 8,895,055 B2

TELODENDRIMER NANODISCS WITHOUT APOLIPOPROTEIN

CROSS-REFERENCES TO RELATED APPLICATIONS

This application claims priority to U.S. Provisional Application No. 61/578,568, filed Dec. 21, 2011, which is incorporated in its entirety herein for all purposes.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Amphotericin B (AmB) is a polyene antifungal agent, first isolated by Gold, et al. from *Streptomyces nodosus* in 1955. It is an amphoteric compound composed of a hydrophilic polyhydroxyl chain along one side and a lipophilic polyene hydrocarbon chain on the other. Amphotericin B is poorly soluble in water (Terrell, C. L. and C. E. Hughes, *Mayo Clin Proc*, 1992. 67(1): 69-91). Commonly, the use of AmB has been limited by its toxicity profile, and especially by hypersensitivity reactions and nephrotoxicity (Gafter-Gvili, A., et al., *Mayo Clin Proc*, 2008. 83(9): 1011-21). Infusion related hypersensitivity is one of the most common adverse events associated with AmB treatment. A series of acute reactions such as high fever, chills, hypotension and tachycardia are often noted shortly (1 to 3 hours) after the amphotericin infusion. Premedication with diphenhydramine and acetaminophen are often indicated for preventing and alleviating these symptoms. Nephrotoxicity is another major side effect. AmB induced nephrotoxicity is dose limiting, and it can be severe and irreversible. Clinical manifestations include azotemia, decreased glomerular filtration, loss of urinary concentrating ability, loss of renal electrolytes, and renal tubular acidosis (Meyer, R. D. *Clin Infect Dis*, 1992. 14: S154-60). In addition, AmB is known to cause anemia, which is thought to be due to a reduction of erythropoietin production (Lin, A. C., et al. *J Infect Dis*, 1990. 161(2): 348-51). Currently, amphotericin B is available in four formulations: amphotericin B deoxycholate (Fungizone®), amphotericin lipid complex (ABLC), amphotericin B colloidal dispersion (ABCD), and liposomal amphotericin (AmBisome® or L-AMB). In general, the lipid formulations of AmB demonstrate better tolerability, and they display significantly different plasma pharmacokinetics (Vogelsinger, H., et al. *J Antimicrob Chemother*, 2006. 57(6): 1153-60).

Recently, a novel lipid formulation of AmB was reported. AmB was incorporated into water-soluble, nanometer-scale reconstituted high-density lipoprotein-like particles, termed nanodiscs (ND). AmB-ND particles have a phospholipid bilayer, with edges stabilized by apolipoprotein to form a disk-shaped structure. The AmB-ND formulation exhibited potent in vitro and in vivo antifungal activity. However, the protein-containing nanodiscs suffer from drawbacks including increased production cost and risk of bacterial toxin contamination associated with the use of recombinant apolipoprotein (Oda, M. N., et al. *J Lipid Res*, 2006. 47(2): 260-7; Tufteland, M., et al. *Peptides*, 2007. 28(4): 741-6), the propensity for apolipoprotein to target hepatocytes, as well as a tendency for such AmB-ND to aggregate which limits clinical applications. Therefore, a need exists for improved formulations for drug delivery in general, as well as for more stable and convenient lipid-based formulations in particular. Surprisingly, the invention as described herein addresses these and other needs.

BRIEF SUMMARY OF THE INVENTION

In one aspect, the present invention provides a nanodisc without a membrane scaffold protein. The nanodisc includes a telodendrimer and a lipid, wherein the nanodisc does not include a membrane scaffold protein.

In a second aspect, the present invention provides a method of making a nanodisc without a membrane scaffold protein. The method includes forming a reaction mixture containing a lipid and a telodendrimer, wherein the lipid:telodendrimer ratio is from about 50:1 to about 1:50 (w/w), thereby preparing the nanodisc without a membrane scaffold protein.

In a third aspect, the present invention provides a nanodisc without a membrane scaffold protein, wherein the nanodisc consists essentially of a telodendrimer, a lipid, and a drug, wherein the ratio of lipid to telodendrimer is from about 50:1 to about 1:50 (w/w). The telodendrimer has the formula PEG-L-D-(R)$_n$, wherein: D is a dendritic polymer having a single focal point group, a plurality of branched monomer units X and a plurality of end groups; L is a bond or a linker linked to the focal point group of the dendritic polymer; each PEG is a polyethyleneglycol (PEG) polymer, wherein each PEG polymer has a molecular weight of 1-100 kDa; each R is independently selected from the group consisting of the end group of the dendritic polymer, a hydrophobic group, a hydrophilic group, an amphiphilic compound and a drug, such that when R is not an end group each R is linked to one of the end groups; and subscript n is an integer from 2 to 20, wherein subscript n is equal to the number of end groups on the dendritic polymer, and wherein at least half the number n of R groups are each an amphiphilic compound.

BRIEF DESCRIPTION OF THE DRAWINGS

FIG. 1 shows the structures and properties of lipids suitable for use in the present invention.

FIG. 2(A) shows an AmB-DPPC mixture before dialysis. FIG. 2 (B) shows AmB-DPPC without (left) and with (right) telodendrimer PEG$^{5k}$CA$_8$ after dialysis. FIG. 2 (C) shows an SN38-DPPC mixture without (left) and with (right) PEG$^{5k}$CA$_8$.

FIG. 3(A-B) shows the disc-shaped structure of an SN38-DPPC-PEG$^{5k}$CA$_8$ mixture as observed by transmission electron microscopy (TEM) images of FIG. 3(C) shows the size distribution of SN38-DPPC-PEG$^{5k}$CA$_8$ as measured by dynamic light scattering (DLS).

FIG. 4 shows the disc-like structure of AmB-MPPG-PEG$^{5k}$CA$_8$ as observed by cryo-electron microscopy at low magnification (A) and high magnification (B).

FIG. 5(A-B) shows the change of solution turbidity after the addition of AmB to phospholipid with or without telodendrimer. FIG. 5(A) shows MPPC in PBS (left), MPPC/AmB in PBS (middle), and MPPC/AmB with telodendrimer PEG$^{5k}$CA$_8$ (right). FIG. 5(B) shows MPPG in PBS (left), MPPG/AmB mixture (middle), and MPPG/AmB with PEG$^{5k}$CA$_8$ (right). FIG. 5(C) shows the size distribution of MPPG/AmB with PEG$^{5k}$CA$_8$ to be 44.7±24.1 nm, with lipid to-telodendrimer (w/w) ratio of 2.5:2.

FIG. 6(A) shows AmB-MPPC-PEG$^{2k}$CA$_4$ nanoformulations with lipid-to-telodendrimer (w/w) ratios of 5:2 (left) and 2.5:2 (right). FIG. 6(B) shows AmB-MPPC-PEG$^{5k}$CA$_8$ (left) and AmB-MPPC-PEG$^{2k}$CA$_4$ (right) with the same lipid-to-telodendrimer (w/w) ratio (2.5:2).

DETAILED DESCRIPTION OF THE INVENTION

I. General

Figure 7:
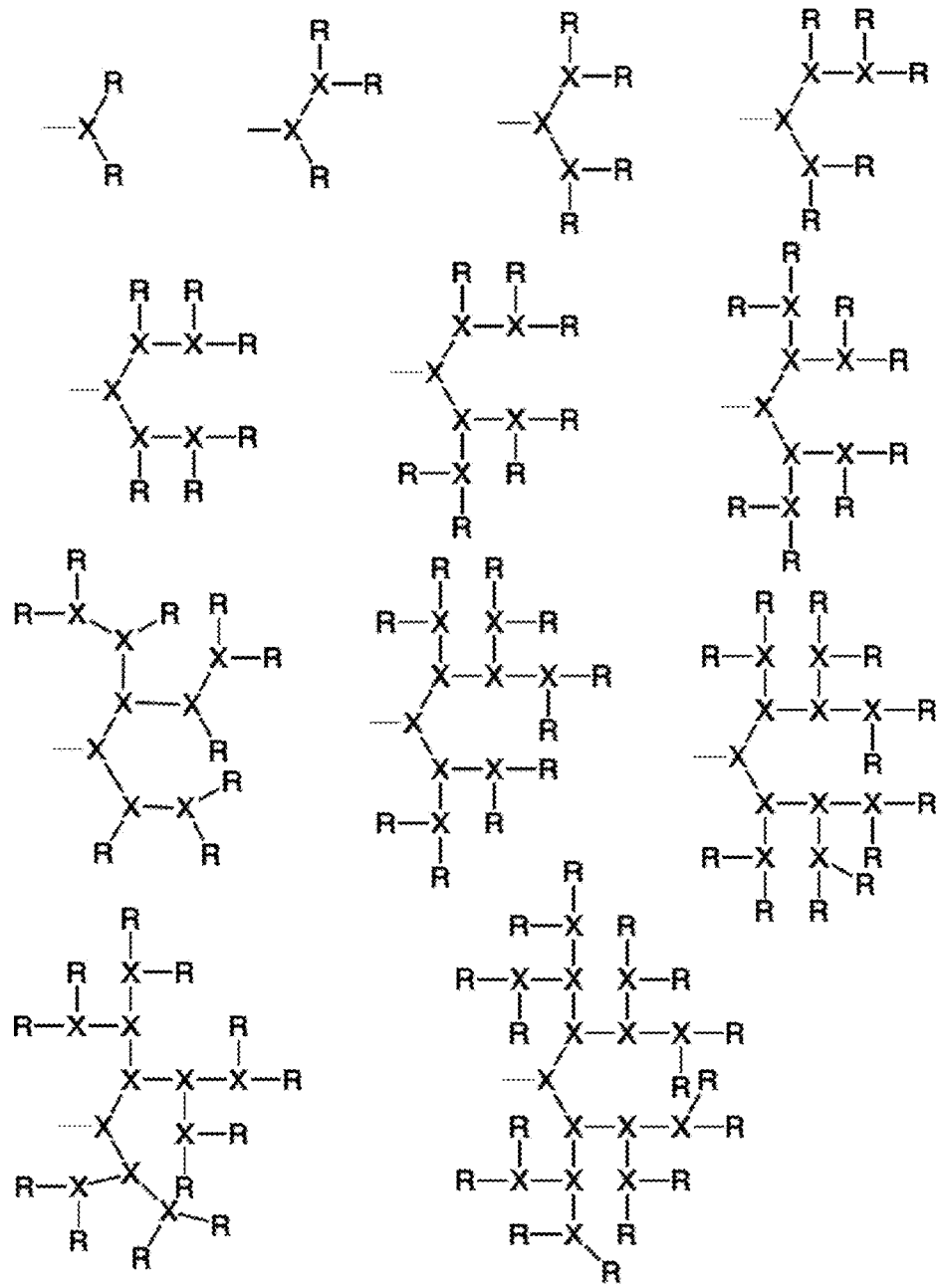
FIG. 7 shows various architectures for the D-(R)$_n$ segment of the telodendrimers useful in the present invention.

The present invention is based on the surprising discovery that amphiphilic polymer conjugates, called "telodendrimers," can bind and stabilize phospholipid bilayers to provide discrete nanostructures termed hybrid nanodiscs (hybrid-ND) without the need for a membrane scaffold protein. The nanodiscs have good loading capability for amphiphilic and hydrophobic drugs such as AmB and SN38 (the active metabolite of irinotecan), superior loading efficiency compared to micelles and liposomes, and superior stability compared to the parent compound. The telodendrimers of the present invention are block copolymers having a linear poly(ethylene glycol) (PEG) segment and a dendritic hydrophobic segment or a dendritic amphiphilic segment. Telodendrimer can also have additional functional groups such as cholic acid groups and hydrophobic drugs covalently bound to the dendritic segment. The telodendrimers can stabilize the formation of lipid bilayer nanodiscs and spherical nanoparticles, eliminating the need for incorporation of apolipoproteins. The invention also provides convenient methods for nanodisc generation.

Nanodisc formulations can be used for delivery of AmB and other drugs, improving drug stability and increasing drug circulation time in the bloodstream. The nanodiscs may also be used to assemble immunogens (e.g. T-cell and B-cell epitopes) and immunomodulating agents (e.g. IL-2, IL-12, interferon-gamma, CpG) for tumor immunotherapy, and for the preparation of tumor vaccines and vaccines against infectious agents. The nanodiscs may also be used for cell-free production of membrane proteins and isolation of the proteins as soluble entities. Incorporation of membrane receptor proteins in the nanodiscs may provide powerful tools for screening of protein ligands/inhibitors for drug discovery.

II. Definitions

As used herein, the term "nanodisc" refers to at least one phospholipid bilayer that is stabilized by a lipid-binding species. The preferred lipid binding species is a telodendrimer as disclosed herein, although other lipid-binding species (including proteins and peptides) are known. The nanodiscs of the present invention are less than one micron in diameter. The nanodiscs can optionally contain additional lipid components, drugs, proteins that are not membrane scaffold proteins, diagnostic agents, and targeting agents.

As used herein, the term "membrane scaffold protein" refers to a protein that can stabilize a phospholipid bilayer in a nanodisc by binding to the bilayer periphery. In general, membrane scaffold proteins have hydrophobic faces that can associate with the nonpolar interior of a phospholipid bilayer and hydrophilic faces that favorably interact with a polar solvent such as an aqueous buffer. Membrane scaffold protein sequences may be naturally occurring, or may be engineered using recombinant techniques or constructed de novo. Naturally occurring membrane scaffold proteins include apolipoproteins, which are components of lipoproteins. Known classes of apolipoproteins include: A (including, for example, apo A-I and apo A-II), B, C, D, E, and H. As used herein, the term "membrane scaffold protein" is not intended to encompass various functional membrane proteins including, but not limited to, ion channels and other transmembrane receptors, porins, certain cell adhesion molecules, and electron transport proteins such as NADH dehydrogenase and ATP synthases.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at a desired end groups using orthogonal protecting group strategies.

As used herein, the term "lipid" refers to lipid molecules that can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like, as described in detail below. Lipids can form micelles, monolayers, and bilayer membranes. The lipids can self-assemble in combination with other components to form nanodiscs.

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendritic polymer can be attached to other segments of the telodendrimers, and the end groups may be further functionalized with additional chemical moieties.

As used herein, the terms "monomer" and "monomer unit" refer to repeating units that make up the dendrons of the dendritic polymers of the invention. The monomers may be AB2-type monomers, where A and B are two different functional groups capable of reacting together such that the resulting polymer chain has a branch point where an A-B bond is formed. Exemplary monomers include a diamino carboxylic acid, a dihydroxy carboxylic acid and a hydroxylamino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl)pentanoic acid. Examples of dihydroxy carboxylic acid groups of the present invention include, but are not limited to, glyceric acid, 2,4-dihydroxybutyric acid, and 2,2-bis(hydroxymethyl)propionic acid. Examples of hydroxylamino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as β-amino acids and other non-naturally occurring amino acids.

As used herein, the term "linker" refers to a chemical moiety that links one segment of a telodendrimer to another. The types of bonds used to link the linker to the segments of the dendrimers include, but are not limited to, amides, amines, esters, carbamates, ureas, thioethers, thiocarbamates, thiocarbonates and thioureas. One of skill in the art will appreciate that other types of bonds are useful in the present invention.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as poly(ethylene glycol) (PEG).

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives.

As used herein, the term "cholic acid" refers to (R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoic acid. Cholic acid is also know as 3α,7α,12α-trihydroxy-5β-cholanoic acid; 3-α,7-α,12-α-Trihydroxy-5-β-cholan-24-oic acid; 17-β-(1-methyl-3-carboxypropyl)etiocholane-3α,7α,12α-triol; cholalic acid; and cholalin. Cholic acid derivatives and analogs, such as allocholic acid, pythocholic acid, avicholic acid, deoxycholic acid, and chenodeoxycholic acid are also useful in the present invention. Cholic acid derivatives can be designed to modulate the properties of the nanodiscs resulting from telodendrimer assembly, such as stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. Drugs useful in the present invention include, but are not limited to, paclitaxel, doxorubicin, etoposide, irinotecan, SN-38, cyclosporin A, podophyllotoxin, Carmustine, Amphotericin B, Ixabepilone, Patupilone (epothelone class), rapamycin and platinum drugs. The drugs of the present invention also include prodrug forms. One of skill in the art will appreciate that other drugs are useful in the present invention.

As used herein, "forming a reaction mixture" refers to combining at least one telodendrimer, at least one phospholipid, and optionally one or more additional components such that they can assemble into lipid-telodendrimer aggregates including nanodiscs. Forming the reaction mixture can include dissolution or suspension of the components in a suitable solvent or mixture of solvents. Forming the reaction mixture can also include forming a dried lipid-containing film and swelling or dispersing the film in a suitable solvent or mixture of solvents.

As used herein, the term "solvent mixture" refers to a mixture of two or more solvents selected for suspension and/or dissolution of nanodisc components in a reaction mixture. The solvents in the mixture and the volume ratio in which they are combined depend primarily on the polarity of the lipids and telodendrimers in the reaction mixture. Non-limiting examples of solvents for use in the solvent mixture include chloroform, dichloromethane, ethanol, methanol, acetone, hexanes, petroleum ether, diethyl ether, dioxane, tetrahydrofuran, and water.

As used herein, the term "lyophilizing" refers to the process of removing one or more solvents from a frozen mixture under vacuum via sublimation. The process typically yields a solvent-free lyophilized mixture. Lyophilization may be conducted at any temperature and pressure sufficient to remove the solvent from a given mixture.

As used herein, the term "contacting" refers to the process of bringing into contact at least two distinct species such that they can react to form covalent bonds or otherwise associate via electrostatic interactions, hydrogen bonding, or van der Waals interactions. In some cases, contacting a species with a solvent includes the dissolving or dispersing the species in a solvent.

III. Telodendrimers

Telodendrimers useful in the present invention include any telodendrimer having a polyethyleneglycol (PEG) polymer linked to a dendrimer functionalized with a hydrophobic group, a hydrophilic group, an amphiphilic compound or a drug on the dendrimer periphery. In some embodiments, the invention provides a compound of formula I:

$$(PEG)_m\text{-}(A)_p\text{-}L\text{-}D\text{-}(R)_n \qquad (I)$$

wherein radical D of formula I is a dendritic polymer having a single focal point group, a plurality of branched monomer units X and a plurality of end groups. Radical L of formula I is a bond or a linker linked to the focal point group of the dendritic polymer. Each PEG of formula I is a polyethyleneglycol (PEG) polymer, wherein each PEG polymer has a molecular weight of 1-100 kDa. Each R of formula I is independently the end group of the dendritic polymer, a hydrophobic group, a hydrophilic group, an amphiphilic compound or a drug, such that when R is not an end group each R is linked to one of the end groups. Subscript n of formula I is an integer from 2 to 20, wherein subscript n is equal to the number of end groups on the dendritic polymer, and wherein at least half the number n of R groups are each independently a hydrophobic group, a hydrophilic group, an amphiphilic compound or a drug. Subscript m of formula I is from 0 to 20. Subscript p is 0 or 1. Radical A of formula I is a monomer or oligomer linked to at least two PEG groups.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxylamino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid or 5-amino-2-(3-aminopropyl)pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine.

The focal point of a telodendrimer or a telodendrimer segment may be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. See, for example, the structures in FIG. 7. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The R groups installed at the telodendrimer periphery can be any suitable chemical moiety, including hydrophilic groups, hydrophobic groups, or amphiphilic compounds. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoic acid, having the structure:

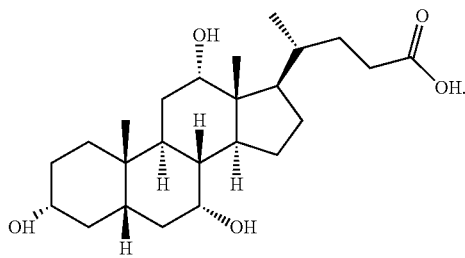

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

Telodendrimer end groups can also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

In some embodiments, each R can be cholic acid, $(3\alpha,5\beta,7\alpha,12\alpha)$-7,12-dihydroxy-3-(2,3-dihydroxy-1-propoxy)-cholic acid, $(3\alpha,5\beta,7\alpha,12\alpha)$-7-hydroxy-3,12-di(2,3-dihydroxy-1-propoxy)-cholic acid, $(3\alpha,5\beta,7\alpha,12\alpha)$-7,12-dihydroxy-3-(3-amino-2-hydroxy-1-propoxy)-cholic acid, cholesterol formate, doxorubicin, or rhein.

The telodendrimer can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, all the R groups are an amphiphilic group such as cholic acid. In other embodiments, some of the R groups are an end group of the dendrimer. In some other embodiments, at least two different R groups are present, such as two different amphiphilic groups, or an amphilic group and a drug, or an amphiphilic group and a dendritic polymer end group, or two different drugs, or a drug and a dendritic end group.

In some embodiments, subscript m is 0. In other embodiments, subscript m is 1. In some other embodiments, subscript m is from 2 to 20.

In some embodiments, subscript p is 0. In other embodiments, subscript p is 1. In some other embodiments, both subscripts m and p are 0. In still other embodiments, subscript m is 1 and subscript p is 0. In yet other embodiments, subscript m is from 2 to 20 and subscript p is 1.

Various telodendrimer architectures are possible. For example, the telodendrimer can have any of the following formulas:

$$PEG-D-(R)_n \qquad (Ia)$$

$$PEG-L-D-(R)_n \qquad (Ib)$$

$$(PEG)_m-A-L-D-(R)_n \qquad (Ic)$$

wherein subscript m of formula Ic is from 2 to 20.

In some embodiments, the telodendrimer can have any of the following formulas:

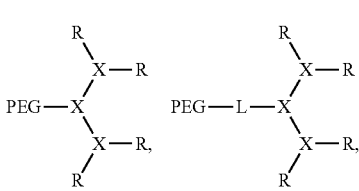

-continued

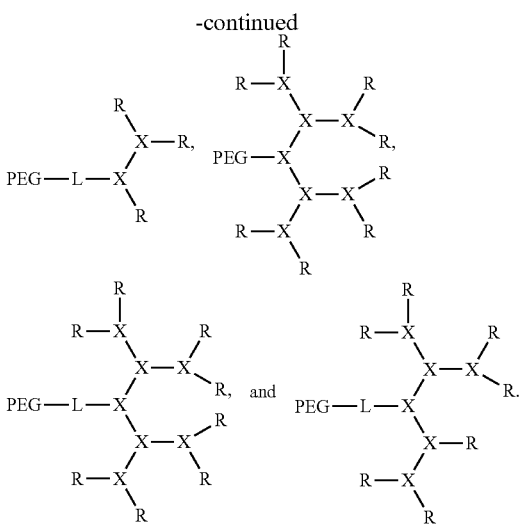

In some embodiments, the telodendrimer can have either of the formulas:

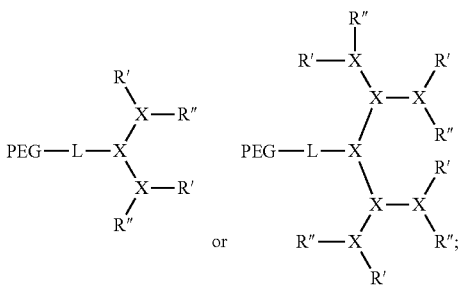

wherein each branched monomer unit X is lysine; and R' and R" are each independently the end group of the dendritic polymer, a hydrophobic group, a hydrophilic group, an amphiphilic compound or a drug, such that R' and R" are different. In some embodiments, each R' can be cholic acid (CA), (3α,5β,7α,12α)-7,12-dihydroxy-3-(2,3-dihydroxy-1-propoxy)-cholic acid (CA-4OH), (3α,5β,7α,12α)-7-hydroxy-3,12-di(2,3-dihydroxy-1-propoxy)-cholic acid (CA-5OH) or (3α,5β,7α,12α)-7,12-dihydroxy-3-(3-amino-2-hydroxy-1-propoxy)-cholic acid (CA-3OH—NH$_2$); and each R" can be cholesterol formate (CF), doxorubicin (DOX), and rhein (Rh).

In some embodiments, the telodendrimer has the formula:

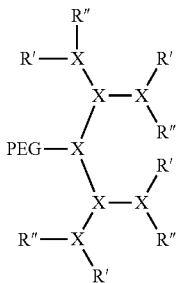

wherein each X is lysine; PEG is PEG5 k; and each R' and R" is CA-4OH, or each R' and R" is CA-5OH, or each R' and R" is CA-3OH—NH$_2$.

In some embodiments, the telodendrimer has the formula:

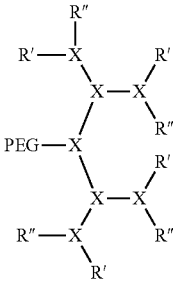

wherein each X is lysine. Each R' is linked to the lysine a amine and each R" is linked to the lysine ε amine. PEG is PEG5 k. Each R' is CA, and each R" is CF; or each R' is CF, and each R" is CA; or each R' and R" is Rh; or each R' is CA, and each R" is Rh; or each R' is Rh, and each R" is CA.

In some embodiments, the telodendrimer has the formula:

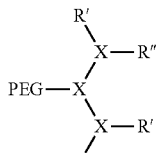

wherein each X is lysine; PEG is PEG (10 k); and each R' and R" is DOX.

The linker L can include any suitable linker. In general, the linkers are bifunctional linkers, having two functional groups for reaction with each of two telodendrimer segments. In some embodiments, the linker can be a heterobifunctional linker. In some embodiments, the linker can be a homobifunctional linker. In some embodiments, the linker L can be polyethylene glycol, polyserine, polyglycine, poly(serine-glycine), aliphatic amino acids, 6-amino hexanoic acid, 5-amino pentanoic acid, 4-amino butanoic acid or beta-alanine. One of skill in the art will recognize that the size and chemical nature of the linker can be varied based on the structures of the telodendrimer segments to be linked.

In some embodiments, linker L has the formula:

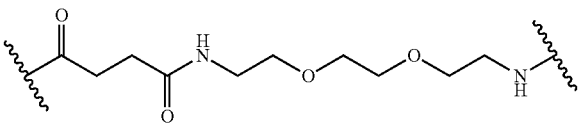 [SMILES: *NCCOCCOCCNC(=O)CCC(*)=O]

Polyethylene glycol (PEG) polymers of any size and architecture are useful in the telodendrimers useful in the present invention. In some embodiments, the PEG is from 1-100 kDa. In other embodiments, the PEG is from 1-10 kDa. In some other embodiments, the PEG is about 3 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention. PEG can be any suitable length.

The bow-tie telodendrimers useful in the present invention contain two branched segments that are linked together at their focal points. Generally, the bow-tie telodendrimers include any telodendrimer as described above or as described previously (WO 2010/039496) and branched PEG segment containing two or more PEG chains bound to an oligomer focal point. Some embodiments of the present invention provide a compound of formula Ic:

wherein D, L, and PEG are described as above. Radical A of formula I is a monomer or oligomer linked to at least two PEG groups. Each R of formula I is independently the end group of the dendritic polymer, a hydrophobic group, a hydrophilic group, an amphiphilic compound or a drug, such that when R is not an end group each R is linked to one of the end groups. Subscript n of formula I is an integer from 2 to 20, wherein subscript n is equal to the number of end groups on the dendritic polymer, and wherein at least half the number n of R groups are each independently a hydrophobic group, a hydrophilic group, an amphiphilic compound or a drug. Subscript m of formula I is an integer from 2 to 20.

In some embodiments, the compound can be:

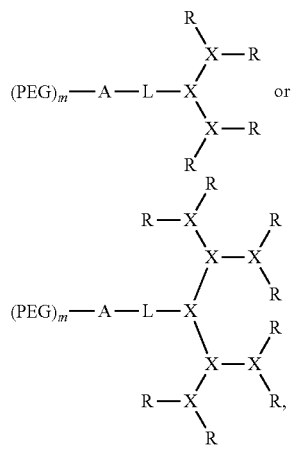

wherein each branched monomer unit X is lysine.

In some embodiments, the compound can be:

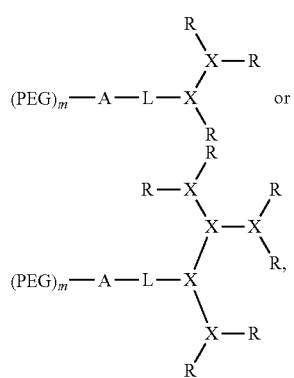

wherein each branched monomer unit X is lysine.

The PEG-oligomer unit in the bow-tie telodendrimers may contain any suitable number of PEG moieties. PEG moieties may be installed site-selectively at various positions on the oligomer using orthogonal protecting groups. In some embodiments, the $(PEG)_m$-A portion of the compound can be:

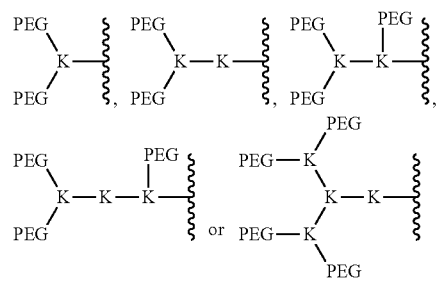

wherein each K is lysine.

In some embodiments, the telodendrimer can be:

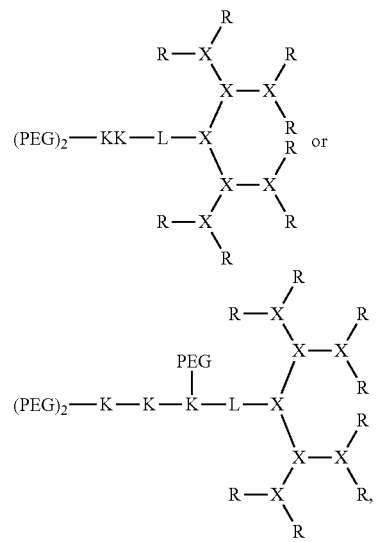

wherein each K is lysine; each PEG is PEG2k; each branched monomer unit X is lysine; each R is cholic acid; and linker L has the formula:

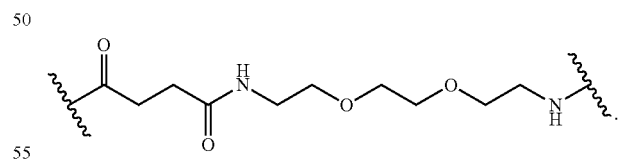

IV. Nanodiscs

As described above, apolipoprotein-containing nanodisc drug formulations have shown in vitro and in vivo activity, but demonstrate limited stability and suffer from the drawbacks associated with the use of recombinant proteins. Telodendrimers offer several advantages over recombinant apolipoprotein when incorporated into the lipid nanodisc formulations. Telodendrimers are synthetic polymers and easy to scale up, without the limitations of cell-based lipoprotein expression and associated biocontaminants. The telodendrimer components (namely PEG and biomolecules including lysine and cholic acid), the telodendrimers, and the telodendrimer-containing nanodiscs are fully biocompatible. The telodendrimer PEG component, presented on the nanodisc surface, reduces particle aggregation due to stacking of the lipid nanodisc. PEGylation can also prevent the rapid clearance of nanodiscs by the reticuloendothelial system, thus providing a sustained delivery of drug to a target site. In addition, the multifunctional telodendrimers allow for the introduction of targeting molecules for specific delivery of drugs to targeted cells, tissues, tumors, or microorganisms. Furthermore, the size and drug loading capacity of the hybrid-ND can easily be tuned by varying the configuration of the telodendrimers, the use of different telodendrimer-lipid combinations or adjusting the ratio of lipid-to-telodendrimer in the final pharmaceutical formulation. Furthermore, functional groups (such as sulhydryl, boronic acid, catechol) can be incorporated into the telodendrimers and lipid head groups so that crosslinking between telodendrimers, lipid head groups and telodendrimer/lipid head group can occur resulting in highly stable but reversible crosslinked nanodiscs.

In one aspect, the present invention provides a nanodisc without a membrane scaffold protein. The nanodisc includes a telodendrimer and a lipid; the nanodisc does not include a membrane scaffold protein.

The telodendrimers that are useful in the present invention are described above and are amphiphilic conjugates having a hydrophilic PEG segment and an amphiphilic or hydrophobic segment. The amphiphilic segment of the telodendrimer can contain cholic acid, or other suitable amphiphilic moiety, which has a hydrophobic face and a hydrophilic face.

The cholic acid and the PEG are connected by dendritic polymers that can contain a variety of acid repeats units. Typically, the dendritic polymers include a diamino carboxylic acid such as lysine.

In some embodiments, the nanodisc includes a telodendrimer having the formula:

PEG-L-D-(R)$_n$ (Ib)

wherein
D is a dendritic polymer having a single focal point group, a plurality of branched monomer units X and a plurality of end groups;
L is a bond or a linker linked to the focal point group of the dendritic polymer;
each PEG is a polyethyleneglycol (PEG) polymer, wherein each PEG polymer has a molecular weight of 1-100 kDa;
each R is independently the end group of the dendritic polymer, a hydrophobic group, a hydrophilic group, an amphiphilic compound or a drug, such that when R is not an end group each R is linked to one of the end groups; and
subscript n is an integer from 2 to 20, wherein subscript n is equal to the number of end groups on the dendritic polymer, and wherein at least half the number n of R groups are each an amphiphilic compound.

In some embodiments, the nanodisc includes a telodendrimer selected from

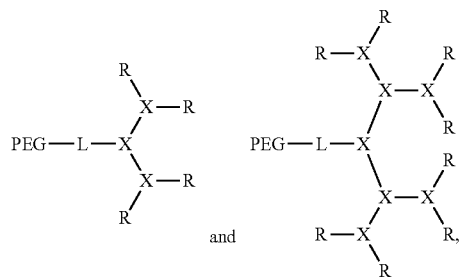

wherein each branched monomer unit X is lysine.

In some embodiments, the nanodisc includes a telodendrimer selected from

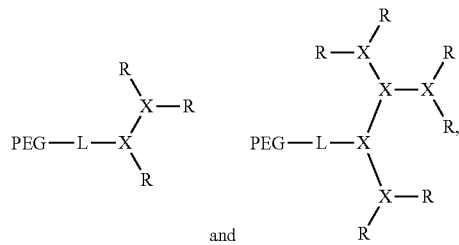

wherein each branched monomer unit X is lysine.

The nanodiscs of the present invention can contain any suitable lipid, including cationic lipids, zwitterionic lipids, neutral lipids, or anionic lipids. Suitable lipids can include fats, waxes, steroids, cholesterol, fat-soluble vitamins, monoglycerides, diglycerides, phospholipids, sphingolipids, glycolipids, cationic or anionic lipids, derivatized lipids, and the like. In some embodiments, the nanodisc contains a lipid selected from a phospholipid, a lysolipid, cholesterol, a phosphatidylcholine, a phosphatidylethanolamine, a phosphatidylglycerol, a phosphatidylserine, a phosphatidylinositol and a PEGylated lipid.

Suitable phospholipids include but are not limited to phosphatidylcholine (PC), phosphatidic acid (PA), phosphatidylethanolamine (PE), phosphatidylglycerol (PG), phosphatidylserine (PS), and phosphatidylinositol (PI), dimyristoyl phosphatidyl choline (DMPC), distearoyl phosphatidyl choline (DSPC), dioleoyl phosphatidyl choline (DOPC), dipalmitoyl phosphatidyl choline (DPPC), dimyristoyl phosphatidyl glycerol (DMPG), distearoyl phosphatidyl glycerol (DSPG), dioleoyl phosphatidyl glycerol (DOPG), dipalmitoyl phosphatidyl glycerol (DPPG), dimyristoyl phosphatidyl serine (DMPS), distearoyl phosphatidyl serine (DSPS), dioleoyl phosphatidyl serine (DOPS), dipalmitoyl phosphatidyl serine (DPPS), dioleoyl phosphatidyl ethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), 1,2-dielaidoyl-sn-glycero-3-phophoethanolamine (transDOPE), and cardiolipin. Phospholipids can be lysolipids, which contain only one fatty acid moiety bonded to the glycerol subunit via an ester linkage. Lipid extracts, such as egg PC, heart extract, brain extract, liver extract, and soy PC, are also useful in the present invention. The lipids can include derivatized lipids, such as PEGylated lipids. Derivatized lipids can include, for example, DSPE-PEG2000, cholesterol-PEG2000, DSPE-polyglycerol, or other derivatives generally known in the art.

Nanodiscs of the present invention can contain steroids, characterized by the presence of a fused, tetracyclic gonane ring system. Examples of steroids include, but are not limited to, cholesterol, cholic acid, progesterone, cortisone, aldosterone, estradiol, testosterone, and dehydroepiandrosterone. Synthetic steroids and derivatives thereof are also contemplated for use in the present invention.

The nanodiscs can contain cationic lipids, which contain positively charged functional groups under physiological conditions. Cationic lipids include, but are not limited to, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N-[1-(2,3,-ditetradecyloxy)propyl]-N,N-dimethyl-N-hydroxyethylammonium bromide (DMRIE), N-[1-(2,3,dioleyloxy)propyl]-N,N-dimethyl-N-hydroxy ethylammonium bromide (DORIE), 3β-[N—(N',N'-dimethylaminoethane) carbamoyl]cholesterol (DC-Chol), dimethyldioctadecylammonium (DDAB) and N,N-dimethyl-2,3-dioleyloxy)propylamine (DODMA).

In some embodiments, the nanodisc of the present invention includes a lipid selected from 1,2-dipalmitoyl-sn-glycero-3-phosphocholine (DPPC), 1,2-ditetradecanoyl-sn-glycero-3-phosphocholine (DMPC), 1-tetradecanoyl-2-hexadecanoyl-sn-glycero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1-tetradecanoyl-2-hexadecanoyl-sn-glycero-3-phosphoglycerol (MPPG) and cholesterol. In some embodiments, the nanodisc contains a lipid selected from MPPG and MPPC.

Any suitable combination of lipids can be used to provide the nanodiscs of the invention. The lipid compositions can be tailored to affect characteristics such as leakage rates, stability, particle size, zeta potential, protein binding, in vivo circulation, and/or accumulation in tissues or organs. For example, negatively or positively lipids, such as DSPG and/or DOTAP, can be included to affect the surface charge of a nanodisc. The lipid compositions can include about ten or fewer types of lipids, or about five or fewer types of lipids, or about three or fewer types of lipids. In some embodiments, the lipid includes at least two different lipids. The molar percentage (mol %) of a specific type of lipid present can be from about 0% to about 10%, from about 10% to about 30%, from about 30% to about 50%, from about 50% to about 70%, from about 70% to about 90%, or from about 90% to 100% of the total lipid present in a nanodisc.

In some embodiments, any of the nanodiscs as described above further include a drug. The drug can be noncovalently sequestered in the nanodisc, covalently linked to a telodendrimer conjugate as an R group as described above, covalently linked to the head group of the lipid, or otherwise associated with the nanodisc. Non-limiting examples of drugs that can be included in the nanodiscs are bortezomib, paclitaxel, SN38, camptothecin, etoposide and doxorubicin, docetaxel, daunorubicin, prednisone, dexamethasone, vincristine, vinblastine, temsirolimus and carmustine. Other suitable drugs include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11) or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; cytarabine (ara-C), doxorubicin, cyclophosphamide, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovorin, oxaliplatin (ELOXATIN™ from Sanofi-Synthelabo Pharmaceuticals, France), Pentostatin, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Raloxifene, Droloxafine, or Hexamethylmelamine. Prodrug forms are also useful in the present invention. Other drugs useful in the present invention also include radionuclides, such as $^{67}$Cu, $^{90}$Y, $^{123}$I, $^{125}$I, $^{131}$I, $^{177}$Lu, $^{188}$Re, $^{186}$Re and $^{211}$At. In some embodiments, the nanodiscs of the present invention include a drug selected from amphotericin B and SN38.

The nanodiscs can also include additional components such as diagnostic agents. A diagnostic agent used in the present invention can include any diagnostic agent known in the art, as provided, for example, in the following references: Armstrong et al., Diagnostic Imaging, 5$^{th}$ Ed., Blackwell Publishing (2004); Torchilin, V. P., Ed., Targeted Delivery of Imaging Agents, CRC Press (1995); Vallabhajosula, S., Molecular Imaging: Radiopharmaceuticals for PET and SPECT, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can also include single photon emission computed tomography (SPECT), magnetic resonance imaging (MRI), optical imaging, positron emission tomography (PET), computed tomography (CT), x-ray imaging, gamma ray imaging, and the like. A diagnostic agent can include chelators that bind to metal ions to be used for a variety of diagnostic imaging techniques. A radioisotope can be incorporated into some of the diagnostic agents described herein and can include radionuclides that emit gamma rays, positrons, beta and alpha particles, and X-rays. The diagnostic agents can include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). The diagnostic agents can include magnetic resonance (MR) and x-ray contrast agents that are known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). The diagnostic agents can be associated with the nanodiscs in a variety of ways including, for example, being covalently bound to a nanodisc component or noncovalently embedded or encapsulated in the nanodisc.

The nanodiscs can also include one or more targeting agents. Generally, a targeting agent can associate with any target of interest, such as a target associated with an organ, tissues, cell, extracellular matrix, or intracellular region. A target can be associated with a particular disease state, such as a cancerous condition. The targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. The target can also be a carbohydrate, such as a monosaccharide, disaccharide, or polysaccharide that can be, for example, present on the surface of a cell. The targeting agent can be a target ligand (e.g., an RGD-containing peptide), a small molecule mimic of a target ligand (e.g., a peptide mimetic ligand), or an antibody or antibody fragment specific for a particular target. Targeting agents can further include folic acid derivatives, B-12 derivatives, NGR derivatives, somatostatin derivatives or peptides that bind to the somatostatin receptor, e.g., octreotide and octreotate, and the like. The targeting agents can also include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., *Trends in Biotech.* 26(8): 442-449 (2008)). The targeting agents can be associated with the nanodiscs in a variety of ways including, for example, being covalently bound to a nanodisc component or noncovalently embedded or encapsulated in the nanodisc. In particular, pathogen-, tissue-, or tumor-specific ligands can be covalently conjugated to the distal end of the PEG segment in the telodendrimer during synthesis to allow for targeted drug delivery.

Any measuring technique available in the art can be used to determine properties of the nanodiscs. For example, techniques such as dynamic light scattering, x-ray photoelectron microscopy, powder x-ray diffraction, scanning electron microscopy (SEM), transmission electron microscopy (TEM), and atomic force microscopy (AFM) can be used to determine average size and dispersity of the nanodiscs. In general, the nanodiscs of the present invention are less than one micron in diameter. The diameter of the nanodiscs can be from about 25 nm to about 900 nm in diameter, or from about 50 nm to about 750 nm in diameter, or from about 100 nm to about 500 nm in diameter. In some embodiments, the nanodisc is less than about 1000 nm in diameter. In some embodiments, the nanodisc is less that about 100 nm in diameter. The diameter of the nanodisc may also be less than 900 nm, or less than 800 nm, or less than 700 nm, or less than 500 nm, or less than 400 nm, or less than 300 nm, or less than 200 nm, or less than 75 nm, or less than 50 nm, or less than 40 nm, or less than 30 nm, or less than 20 nm.

The nanodiscs of the invention may contain any suitable combination of lipids with telodendrimers and/or other components. The ratio of lipid to telodendrimer in the nanodisc, for example, can be from about 100:1 to about 1:100 (w/w). The ratio of lipid to telodendrimer can be from about 75:1 to about 1:75 (w/w), or from about 25:1 to about 1:25 (w/w), or from about 40:1 to about 1:40 (w/w), or from about 30:1 to about 1:30 (w/w), or from about 20:1 to about 1:20 (w/w), or from about 10:1 to about 1:10 (w/w). In some embodiments, the ratio of lipid to telodendrimer in the nanodisc is from about 50:1 to about 1:50 (w/w). In some embodiments, the ratio of lipid to telodendrimer is from about 5:1 to about 1:5 (w/w). In some embodiments, the ratio of lipid to telodendrimer is from about 5:1 to about 1:1 (w/w). Other useful ratios include 4:1, 3:1, 5:2, 2:1, 3:2, 4:3, 5:4, 6:5, 7:6, 8:7, 9:8 and 10:9 (w/w). In some embodiments, the ratio of lipid to telodendrimer is about 5:2 (w/w). In some embodiments, the ratio of lipid to telodendrimer is about 2.5:2 (w/w). Other weight ratios of lipid to telodendrimer can also be useful in the present invention.

Some embodiments of the present invention provide a nanodisc without a membrane scaffold protein consisting essentially of:

a telodendrimer having the formula:

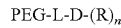

PEG-L-D-(R)$_n$ wherein

D is a dendritic polymer having a single focal point group, a plurality of branched monomer units X and a plurality of end groups, L is a bond or a linker linked to the focal point group of the dendritic polymer, each PEG is a polyethyleneglycol (PEG) polymer, wherein each PEG polymer has a molecular weight of 1-100 kDa, each R is independently the end group of the dendritic polymer, a hydrophobic group, a hydrophilic group, an amphiphilic compound or a drug, such that when R is not an end group each R is linked to one of the end groups, and subscript n is an integer from 2 to 20, wherein subscript n is equal to the number of end groups on the dendritic polymer, and wherein at least half the number n of R groups are each an amphiphilic compound;

a lipid; and a drug, wherein the ratio of lipid to telodendrimer is from about 50:1 to about 1:50 (w/w).

V. Methods of Making Nanodiscs

In some embodiments, the present invention provides a method of making a nanodisc without a membrane scaffold protein. The method includes forming a reaction mixture having a lipid and a telodendrimer, wherein the lipid:telodendrimer ratio is from about 50:1 to about 1:50 (w/w), thereby preparing the nanodisc without a membrane scaffold protein.

Any other suitable combination of lipids with telodendrimers and/or other components, as described above, can also be employed in the methods of the present invention. Still other weight ratios of lipid to telodendrimer may also be useful in the methods of the present invention. The methods may further include incorporation of additional components, such as drugs, diagnostic agents, and targeting agents, as described above, into the reaction mixture.

The reaction mixture generally includes a solvent or a mixture of solvents. In some embodiments, the reaction mixture further includes a solvent mixture. In general, the solvent mixture contains two or more solvents selected to sufficiently solubilize the lipid component and the telodendrimer component of the reaction mixture as well as any additional components. Suitable solvents include, but are not limited to, chloroform, dichloromethane, ethanol, methanol, acetone, hexanes, petroleum ether, diethyl ether, dioxane, tetrahydrofuran, and water. The solvent mixture can be, for example, a mixture of chloroform and ethanol. The chloroform:ethanol ratio in such mixtures can be from about 100:1 to about 1:1 (v/v), or from about 50:1 to about 1:1 (v/v), or from about 25:1 to about 1:1 (v/v), or from about 5:1 to about 1:1 (v/v). In some embodiments, the solvent mixture includes chloroform and ethanol in a chloroform:ethanol ratio of from about 10:1 to about 1:1 (v/v). One of skill in the art will appreciate that mixtures of other solvents in varying ratios may be useful in the methods of the present invention, depending on the polarity of the reaction mixture components.

In some embodiments, the methods of the invention further include lyophilizing the reaction mixture and contacting the lyophilized reaction mixture and a solvent to form a dispersed lipid-telodendrimer mixture. Lyophilization generally includes freezing the reaction mixture followed by removal of the frozen solvent mixture under vacuum. The lyophilization can be conducted at any temperature and pressure sufficient to remove the solvent mixture from the other reaction mixture components. The lyophilized reaction mixture can then be contacted with any of the solvents as described above. The solvent can also be an aqueous buffer optionally containing salts, tonicity modifiers, acids and/or bases for pH adjustment, detergents, organic co-solvents, preservatives, or other components. Upon contact of the lyophilized reaction mixture with the solvent, a dispersed lipid-telodendrimer mixture is formed.

In some embodiments, the method further includes contacting the dispersed lipid-telodendrimer mixture with a drug such that the drug is loaded into the nanodisc. The drug can be included in the solvent prior to contacting the lyophilized reaction mixture, or the drug may be added to the dispersed lipid-telodendrimer mixture after dispersion with the solvent. The dispersed lipid-telodendrimer mixture may be contacted with the drug for any amount of time sufficient to load the drug into the nanodiscs. So-called "passive" loading techniques involve the incorporation of drugs into a nanodisc during the nanodisc self-assembly process in solution, such that the drug is encapsulated or embedded within the nanodisc. Alternatively, the drugs can be actively loaded into nanodiscs. For example, the nanodiscs can be exposed to conditions, such as electroporation, in which the bilayer membrane is made permeable to a solution containing therapeutic agent thereby allowing for the drug to enter into the nanodisc. Loading of the nanodiscs with drugs or other components can be carried out via other methods known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006).

The methods of the invention may optionally include additional steps such as sonication and/or freeze-thaw cycles to aid in dispersion and self-assembly, extrusion to yield nanodiscs with homogenous size and shape, dialysis to remove or exchange soluble species such as unbound drugs and buffer salts, and other steps. These optional steps may occur at any time during the methods of the invention.

VI. Examples

Example 1

Preparation and Characterization of Drug Loaded Hybrid-ND

Materials. Monomethyl-terminated poly(ethylene glycol) monoamine (MeO-PEG-NH$_2$, MW=5 kDa or 2 kDa) was purchased from Rapp Polymere (Tübingen, Germany). (Fmoc)lysine(Fmoc)OH was purchased from NeoMPS INC (San Diego, Calif., USA). Cholic acid was purchased from Sigma-Aldrich (St Louis, Mo.). 1,2-dipalmitoyl-sn-glycero-3-phosphocholine (DPPC), 1,2-ditetradecanoyl-sn-glycero-3-phosphocholine (DMPC), 1-tetradecanoyl-2-hexadecanoyl-sn-glycero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPG), 1,2-dipalmitoyl-sn-glycero-3-phospho-(1'-rac-glycerol) (DPPG), 1-tetradecanoyl-2-hexadecanoyl-sn-glycero-3-phosphoglycerol (MPPG) and cholesterol were purchased from Avanti Polar Lipids, Inc. (Alabaster, Ala.). Amphotericin B was purchased from Sigma-Aldrich (St Louis, Mo.).

Synthesis of PEG$^{5k}$-CA$_8$ and PEG$^{2k}$-CA$_4$ Telodendrimers. PEG$^{5k}$-CA$_8$ and PEG$^{2k}$-CA$_4$ were synthesized via solution phase condensation reactions from MeO-PEG-NH$_2$ with a molecular weight of 5000 Dalton and 2000 Dalton respectively. (Fmoc)-lysine (Fmoc)-OH (2 eq.) was coupled onto the N terminal of PEG using DIC (2 eq.) and HOBt (2 eq.) as coupling reagents in DMF for overnight. The completion of the coupling was monitored by Kaiser test. PEGylated molecules were precipitated by adding cold ether and washed with ether twice. Fmoc groups were removed by treatment with 20% piperidine in DMF, and the PEGylated molecules were precipitated and washed three times with cold ether. White powder precipitate was dried under vacuum and another two repeat couplings of (Fmoc)-lysine(Fmoc)-OH were carried out to generate a third generation of dendritic polylysine on one terminus of PEG. Cholic acid NHS ester was coupled to the terminal end of dendritic polylysine, resulting in PEG$^{5k}$-CA$_8$ and PEG$^{2k}$-CA$_4$. These telodendrimers were subsequently dialyzed and lyophilized to yield a dry white powder.

Preparation of Drug Loaded Hybrid-ND. Phospholipids (DPPC, DMPC, MPPC, DSPC, DSPE, DPPE, DSPG, MPPC, MPPG or cholesterol; 2.5 or 5 mg) were first combined with telodendrimer (2 mg), and dissolved in 1 mL of chloroform/ethanol 3:1 v/v mixture. The mixture was dried under a stream of nitrogen gas until a homogeneous coating on the inner surface of the glass tube was formed. The tube was vacuumed under a mechanical pump for at least 3 hours. Phosphate buffered saline (PBS) 1 ml was added to disperse the lipid-telodendrimer, followed by a 20-minute sonication. To the dispersed lipid-telodendrimer mixture, AmB or SN38 stock solution (30 mg/ml in DMSO), 42 µL and 50 µL respectively, were added. The AmB-lipid-telodendrimer mixture was sonicated for 60 minutes at 37° C. to allow complete dissolution. The final solution was dialyzed for 24 to 48 hours against PBS to remove residual DMSO.

Particle Size Distribution and Drug Loading. A dynamic light scatter analyzer (Zetatrac®, Microtrac, USA) was used to measure the particle size distribution of the hydrid-ND loaded with amphotericin B and SN38. The concentration of the drug loaded to the hybrid-ND was quantified by UV spectrometry (NanoDrop2000 spectrophotometer. Thermo Scientific, USA).

Morphological Characteristics. The morphology of the drug loaded hybrid-ND was investigated by transmission electron microscopy (TEM) and cryo-electron microscopy (cryo-EM).

Characterization of Hybrid-HD. The addition of telodendrimer changed the turbidity and physical property of the drug-lipid mixture, and resulted in a more stable and homogeneous solution (FIG. 2). Using dynamic light scattering analysis, the mean size distributions of several AmB-hybrid-NDs and SN38-DPPC hybrid-ND were measured to be 50 to 200 nm (Table 1, below) and 120 nm (FIG. 3C), respectively. The size of the hybrid-ND particle varies depending on the composition. TEM and cryo-EM images of AmB-hybrid-ND and SN38-hybrid-ND showed a disc-like structure as shown in FIG. 3 and FIG. 4. The size, drug loading capacity, and other properties of the hybrid-ND can easily be tuned by varying the configuration of the telodendrimers, the use of different telodendrimer-lipid combinations, or adjusting the ratio of lipid-to-telodendrimer in the final pharmaceutical formulation (FIG. 6).

TABLE 1

Particle sizes for various Amphotericin (AmB) hybrid-ND compositions.[a]

| Phospholipids (PL) | AmB:PL:PEG$^{2k}$CA$_4$ (w/w) | | AmB:PL:PEG$^{5k}$CA$_8$ (w/w) | |
|---|---|---|---|---|
| | 1.25:2.5:2 | 1.25:5:2 | 1.25:2.5:2 | 1.25:5:2 |
| MPPG | ppt | ppt | ppt | 116.1 ± 50.9 |
| MPPC | 56 ± 27.8 | ppt | ppt | 116.1 ± 55.4 |
| DPPC | ppt | ppt | ppt | ppt +++/gel |
| DMPC | ppt | ppt | ppt | ppt |
| DPPG | ppt | ppt | ppt | ppt |

[a]Particle size = diameter in nanometers.
ppt = precipitate.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A nanodisc without a membrane scaffold protein, the nanodisc comprising:
   a telodendrimer of formula I:

(PEG)$_m$-(A)$_p$-L-D-(R)$_n$      (I)

wherein
   D is a dendritic polymer having a single focal point group, a plurality of branched monomer units and a plurality of end groups,
   L is a bond or a linker linked to the focal point group of the dendritic polymer,
   each PEG is a polyethyleneglycol (PEG) polymer, wherein each PEG polymer has a molecular weight of 1-100 kDa,
   each R is independently selected from the group consisting of the end group of the dendritic polymer, a hydrophobic group, a hydrophilic group, an amphiphilic compound and a drug, such that when R is not an end group each R is linked to one of the end groups,
   subscript n is an integer from 2 to 20, wherein subscript n is equal to the number of end groups on the dendritic polymer, and wherein at least half the number n of R groups are each independently selected from the group consisting of a hydrophobic group, a hydrophilic group, an amphiphilic compound and a drug,
   subscript m is from 0 to 20,
   subscript p is 0 or 1, and
   radical A is a monomer or oligomer linked to at least two PEG groups; and
   a lipid,
   wherein the nanodisc does not include a membrane scaffold protein.

2. The nanodisc of claim 1, wherein the telodendrimer has the formula Ib:

PEG-L-D-(R)$_n$      (Ib)

wherein at least half the number n of R groups
   are each an amphiphilic compound.

3. The nanodisc of claim 2, wherein each branched monomer unit is lysine.

4. The nanodisc of claim 2, wherein the telodendrimer is selected from the group consisting of:

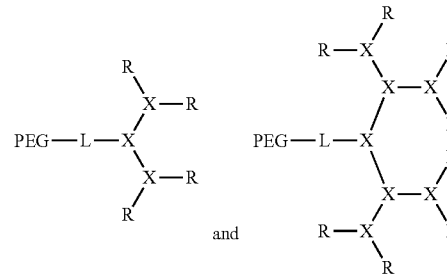

and wherein each branched monomer unit X is lysine.

5. The nanodisc of claim 2, wherein linker L has the formula:

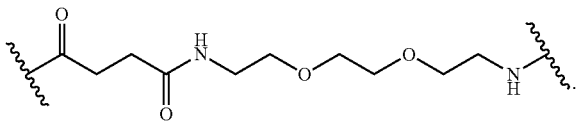 [SMILES: *NCCOCCOCCNC(=O)CCC(*)=O]

6. The nanodisc of claim 2, wherein each R is independently selected from the group consisting of cholic acid, (3α,5β,7α,12α)-7,12-dihydroxy-3-(2,3-dihydroxy-1-propoxy)-cholic acid (CA-4OH), (3α,5β,7α,12α)-7-hydroxy-3,12-di(2,3-dihydroxy-1-propoxy)-cholic acid (CA-5OH), (3α,5β,7α,12α)-7,12-dihydroxy-3-(3-amino-2-hydroxy-1-propoxy)-cholic acid (CA-3OH—NH$_2$), cholesterol formate, doxorubicin, and rhein.

7. The nanodisc of claim 2, wherein each R is cholic acid.

8. The nanodisc of claim 2, wherein the telodendrimer is selected from the group consisting of PEG$^{5k}$-D-CA$_8$ and PEG$^{2k}$-D-CA$_4$, wherein each dendritic polymer D is a poly(lysine) dendritic polymer.

9. The nanodisc of claim 1, wherein the lipid is selected from the group consisting of a phospholipid, a lysolipid., cholesterol, a phosphatidylcholine, a phosphatidylethanolamine, a phosphatidylglycerol, a phosphatidylserine, a phosphatidylinositol and a PEGylated lipid.

10. The nanodisc of claim 9, wherein the lipid is selected from the group consisting of 1,2-dipahnitoyl-sn-glycero-3-phosphocholine (DPPC), 1,2-ditetradecanoyl-sn-glycero-3-phosphocholine (DMPC), 1-tetra.decanoyl-2-hexadecanoyl-sn-glyeero-3-phosphocholine (MPPC), 1,2-dioctadecanoyl-sn-glycero-3-phosphocholine (DSPC), 1,2-distearoyl-sn-glycero-3-phosphoethanolamine (DSPE), 1,2-dihexadecanoyl-sn-glycero-3-phosphoethanolamine (DPPE), 1,2-distearoyl-sn-glycero-3-phospho-(1'-rac-glycerol) (DSPG), 1,2-dipalmitoyi-sn-glycero-3-phospho-1'-rac-glycerol) (DPPG),1-tetradecanoyl-2-hexadecanoyl-sn-glycero-3-phosphoglycerol (MPPG) and cholesterol.

11. The nanodisc of claim 10, wherein the lipid is selected from the group consisting of MPPG and MPPC.

12. The nanodisc of claim 1, further mprising a drug.

13. The nanodisc of claim 1, wherein the nanodisc is less than about 100 run in diameter.

14. The nanodisc of claim 1, wherein the ratio of lipid to telodendrimer is from about 5:1 to about 1:1 (w/w).

15. The nanodisc of claim 1, wherein the ratio of lipid to telodendrimer is about 2.5:2 (w/w).

16. A method of making a nanodisc without a membrane scaffold protein, the method comprising:
forming a reaction mixture comprising a lipid and a telodendrimer, wherein the lipid:telodendrimer ratio is from about 50:1 to about 1:50 (w/w), thereby preparing the nanodisc without a membrane scaffold. protein, wherein the telodendrimer is of formula I:

$$(PEG)_m\text{-}(A)_p\text{-}L\text{-}D\text{-}(R)_n \quad (I)$$

wherein
D is a dendritic polymer having a single focal point group, a plurality of branched monomer units and a plurality of end groups,
L is a bond or a linker linked to the focal point of the dendritic polymer,
each PEG is a polyethyleneglycol (PEG) polymer, wherein each PEG polymer has a molecular weight of 1-100 kDa,
each R is independently selected from the group consisting of the end group of the dendritic polymer, a hydrophobic group, a hydrophilic group, an amphiphilic compound and a drug, such that when R is not an end group each R is linked to one of the end groups,
subscript n is an integer from 2 to 20, wherein subscript n is equal to the number of end groups on the dendritic-solymer, and wherein at least half the number n of groups are each independently selected from the group consisting of a hydrophobic group, a hydrophilic group, an arnphiphi lie compound and a drug,
subscript m is from 0 to 20,
subscript p is 0 or 1, and
radical A is a monomer or oligomer linked to at least two PEG groups.

17. The method of claim 16, wherein the lipid:telodendri ratio is from about 5:1 to about 1:1 (w/w).

18. The method of claim 16, Wherein the lipid:telodendrimer ratio is about 5:2 (w/w).

19. The method of claim 16, the reaction mixture further comprises chloroform and ethanol in a chloroform:ethanol ratio of from about 10:1 to about 1:1 (v/v).

20. The method of claim 16, further comprising
lyophilizing the reaction mixture; and
contacting the lyophilized reaction mixture and a solvent to form a dispersed lipid-telodendrimer mixture.

21. A nanodisc without a membrane scaffold protein, the nanodisc consisting essentially of:
a telodendrimer having the formula:

$$PEG\text{-}L\text{-}D(R)_n$$

wherein
D is a dendritic polymer having a single focal point group, a plurality of branched monomer units and a plurality of end groups,
L is a bond or a linker linked to the focal point group of the dendritic polymer,
each PEG is a polyethyleneglycol (PEG) polymer, wherein each PEG polymer has a molecular weight of 1-100 kDa,
each R is independently selected from the group consisting of the end group of the dendritic polymer, a hydrophobic group, a hydrophilic group, an amphiphilic compound and a drug, such that when R is not an end group each R is linked to one of the end groups, and
subscript n is an integer from 2 to 20, wherein subscript n is equal to the number of end groups on the dendritic polymer, and wherein at least half the number n of R groups are each an amphiphilic compound;
a lipid; and
a drug,
wherein the ratio of lipid to telodendrimer is from about 50:1 to about 1:50 (w/w).

* * * * *